(12) United States Patent
Schultz et al.

(10) Patent No.: US 9,915,608 B2
(45) Date of Patent: Mar. 13, 2018

(54) OPTICAL SENSOR FOR DETERMINING THE CONCENTRATION OF AN ANALYTE

(75) Inventors: Peter Schultz, Saint Thomas, VI (US); Arkady Amosov, Saint Petersburg (RU); Natalia Izvarina, Saint Petersburg (RU); Sergey Kravetz, Ashdod (IL)

(73) Assignee: BioSensor, Inc., Essex, NY (US)

( * ) Notice: Subject to any disclaimer, the term of this patent is extended or adjusted under 35 U.S.C. 154(b) by 1019 days.

(21) Appl. No.: 12/741,350

(22) PCT Filed: Oct. 31, 2008

(86) PCT No.: PCT/US2008/012349
§ 371 (c)(1),
(2), (4) Date: Aug. 4, 2010

(87) PCT Pub. No.: WO2009/061367
PCT Pub. Date: May 14, 2009

(65) Prior Publication Data
US 2011/0105867 A1    May 5, 2011

Related U.S. Application Data

(60) Provisional application No. 61/001,960, filed on Nov. 5, 2007.

(51) Int. Cl.
*A61B 6/00* (2006.01)
*G01N 21/49* (2006.01)
(Continued)

(52) U.S. Cl.
CPC ........... *G01N 21/49* (2013.01); *A61B 5/0059* (2013.01); *A61B 5/1455* (2013.01);
(Continued)

(58) Field of Classification Search
CPC ................ A61B 5/0084; A61B 5/0059
(Continued)

(56) References Cited

U.S. PATENT DOCUMENTS

| 4,573,761 | A | * | 3/1986 | McLachlan et al. | ......... 385/115 |
| 5,657,754 | A | * | 8/1997 | Rosencwaig | ................. 600/316 |

(Continued)

FOREIGN PATENT DOCUMENTS

| CN | 1184936 A | 6/1998 |
| CN | 1600271 A | 3/2005 |

(Continued)

OTHER PUBLICATIONS

International Search Report and Written Opinion dated Feb. 9, 2009, Application No. PCT/US2008/012349.
(Continued)

*Primary Examiner* — Tse Chen
*Assistant Examiner* — Hien Nguyen
(74) *Attorney, Agent, or Firm* — Finnegan, Henderson, Farabow, Garrett & Dunner LLP.

(57) ABSTRACT

A method and apparatus for non-invasively determining a concentration of glucose in a subject using optical excitation and detection is provided. The method includes emitting an exciter beam (B1) to irradiate a portion (130) of tissue of the subject, causing physical and chemical changes in the surface, and causing an initial back scattering (D1) of light. The method further includes periodically emitting a probe beam (B2) which irradiates the portion of tissue and causes periodic back scatterings (D2) of light. The initial and periodic back scatterings are detected and converted into electrical signals of at least the amplitude, frequency or decay time of the physical and chemical changes, the back scatterings being modulated by the physical and chemical changes. By differentiating over time at least one of the
(Continued)

amplitude, frequency or decay time of the physical and chemical changes, the concentration of glucose may be determined.

45 Claims, 7 Drawing Sheets

(51) Int. Cl.
    *A61B 5/00*     (2006.01)
    *A61B 5/145*     (2006.01)
    *A61B 5/1455*     (2006.01)
    *G01N 21/17*     (2006.01)

(52) U.S. Cl.
    CPC ..... *A61B 5/14532* (2013.01); *G01N 21/1717* (2013.01); *A61B 5/7239* (2013.01); *G01N 2021/1725* (2013.01)

(58) Field of Classification Search
    USPC .......................................................... 600/310
    See application file for complete search history.

(56) References Cited

U.S. PATENT DOCUMENTS

| | | | | |
|---|---|---|---|---|
| 5,941,821 | A * | 8/1999 | Chou | 600/316 |
| 6,049,728 | A * | 4/2000 | Chou | 600/316 |
| 6,097,975 | A * | 8/2000 | Petrovsky et al. | 600/316 |
| 6,675,030 | B2 * | 1/2004 | Ciurczak et al. | 600/316 |
| 2002/0016533 | A1 * | 2/2002 | Marchitto et al. | 600/310 |
| 2005/0010090 | A1 * | 1/2005 | Acosta et al. | 600/316 |
| 2005/0277872 | A1 * | 12/2005 | Colby et al. | 604/67 |
| 2007/0060819 | A1 * | 3/2007 | Altshuler et al. | 600/475 |

FOREIGN PATENT DOCUMENTS

| | | |
|---|---|---|
| EP | 0 843 986 A2 | 5/1998 |
| JP | 2002-514450 A | 5/2002 |
| JP | 2006-231075 A | 9/2006 |
| WO | WO 97/02781 | 1/1997 |

OTHER PUBLICATIONS

Second Chinese Office Action including Search Report issued by the Chinese Patent Office for corresponding application 201110391618.1, dated Apr. 22, 2014.
Office Action including Search Report issued in the Taiwanese Patent Office dated Feb. 17, 2014.
Office Action issued in Japanese Patent Application No. 2010-533075 dated Dec. 3, 2013.
First Office Action and Search Report Issued in Chinese Patent Application No. 201110391618.1 dated Aug. 23, 2013.
Examination Report issued in Australian Patent Application No. 2008325237 dated Apr. 3, 2013.
First Office Action issued in Chinese Patent Application No. 200880124606.9 dated Nov. 24, 2011.
Second Office Action issued in Chinese Patent Application No. 200880124606.9 dated Jun. 20, 2012.
Third Office Action issued in Chinese Patent Application No. 200880124606.9 dated Jan. 18, 2013.
Fourth Office Action issued in Chinese Patent Application No. 200880124606.9 dated May 30, 2013.
Office Action issued in Israeli Patent Application No. 205499 dated May 14, 2012.
Office Action issued in Japanese Patent Application No. 2010-533075 dated Jul. 16, 2013.
Search Report issued in Chinese Patent Application No. 201110391618.1 dated Aug. 15, 2014.
Third Office Action issued in Chinese Patent Application No. 201110391618.1 dated Aug. 27, 2014.

\* cited by examiner

OPTICAL SENSOR FOR DETERMINING THE CONCENTRATION OF AN ANALYTE

RELATED APPLICATION

This application claims priority to U.S. Provisional Patent Application No. 61/001,960, filed Nov. 5, 2007, the contents of which is incorporated herein in its entirety.

TECHNICAL FIELD

The present invention relates to optical material analysis, and determining the concentration of an analyte using optical material analysis.

BACKGROUND

Diabetes mellitus is a serious disease that affects not only a patient's internal organs, circulation system and eyesight, but also a patient's lifestyle. There are reportedly more than 200 million diabetic people in the world at the moment, and this figure is expected to double within the next ten years. The first step in diabetes care is to monitor the patient's blood glucose level 24 hours a day, as knowing the glucose level assists in determining the right diet and medical treatment.

Current methods of measuring blood glucose concentrations typically require the diabetic patient to puncture a finger to collect a drop of blood, whose chemical composition is then analyzed by a glucose meter. As the procedure is not totally painless and harms the skin, diabetic patients are often unwilling to check their glucose level as frequently as their doctors prescribe, and are thus unable to sufficiently monitor their glucose level.

At present, the majority of portable devices for measuring glucose levels require puncturing the fingertip to obtain a blood sample. The blood sample is then placed on a test strip that indicates the glucose concentration. An example is the OneTouch® Ultra® glucose meter sold by LifeScan Inc., a Johnson & Johnson company. These devices are very compact and reasonably accurate, but puncturing the fingertip to obtain a blood sample is inconvenient and can be painful. Moreover, improper puncturing and hygiene may pose a risk of fingertip infection.

As an alternative to the traditional fingertip-puncturing methods, Cygnus Inc. has developed the GlucoWatch® Biographer monitor. The device, which looks like a wristwatch, pulls interstitial body fluid from the skin using small electric currents to extract glucose into a consumable transdermal pad, which acts as an iontophoretic sensor. The collected glucose triggers an electro-chemical reaction in the sensor, generating electrons. The sensor measures the electrons and equates the level of electron emission to a concentration of glucose in the body fluid. This device checks body fluid glucose levels every 20 minutes for up to 12 hours. Following the twelve hour period of operation, the monitor must be calibrated with a finger-prick reading for comparing with blood glucose levels. The device has a relative measuring error that has been determined to be approximately 10-30% in part because the glucose levels of interstitial fluid lags behind blood. However, in order to be able to even purchase one of these devices, a potential buyer must undergo and pass a physical and biochemical examination. Moreover, the device also has been known to severely inflame the skin in some patients with sensitive skin where the electrical currents are introduced.

Because of the lack of success of alternative devices such as GlucoWatch®, other non-invasive measurements have begun to be developed. Many of these alternative non-invasive methods involve using optical methods. Some of these optical methods have shown promise in providing a non-invasive measurement alternative. For example, some optical methods have used non-ionizing radiation to obtain a reading, providing fast responses without the need for consumable reagents. Moreover, as the availability of more sophisticated lasers and optical detectors increase, and the costs associated with using these optical devices decrease, optical methods may become an even more appealing alternative form of non-invasive measurement.

Typical non-invasive optical methods utilize a beam of light to irradiate some selected part of the human body, such as a finger, the forearm, tongue, lip, thigh or abdomen, etc. Light that is transmitted through, reflected, or scattered out of the skin comprises information about the composition of the irradiated tissue. This light is then received by optical detectors and analyzed to determine the concentrations of certain analytes, such as oxygen or hemoglobin. The analysis, however, is inherently complex because the received signal is often very faint and easily interfered with not only by a number of analytes in blood, but also by other factors including the variability and inhomogeneity of the human skin and the constantly changing human physiology, and even the external environment around the skin. Conventional optical methods of material analysis such as absorption and luminescent spectroscopy, Raman spectroscopy, and measuring polarization and reflectance changes are not sufficiently suitable for a turbid medium such as human tissue due to significant diffuse scattering of the reference light beam.

Other non-invasive methods take advantage of the correlation that exists between glucose content in the interstitial fluid and capillary blood, but suffer from the primary disadvantage of being time consuming. Furthermore, they only provide an indirect measure of glucose concentration, which is, unfortunately, also time-delayed.

The technique of laser photoacoustic spectroscopy has been used in trace detection due to the high sensitivity it offers. In the method of laser photoacoustic spectroscopy, a high-energy laser beam is used to irradiate the matter under study. The beam produces a thermal expansion in the matter, thereby generating an acoustic wave. The characteristics of the wave are determined not only by the optical absorption coefficient of the matter, but also by such thermal physical parameters as thermal expansion, specific heat, and sound velocity. In addition, the acoustic wave may also be affected by optical scattering, which influences the distribution of light in the matter that can be measured by high-sensitivity ultrasonic detectors such as piezo-electric crystals, microphones, optical fiber sensors, laser interferometers or diffraction sensors.

For example, U.S. Pat. Nos. 5,941,821 and 6,049,728 to Chou describe a method and apparatus for noninvasive measurement of blood glucose by photoacoustics. Upon irradiation, acoustic energy is generated in a relatively thin layer of the sample to be measured, characterized by a heat-diffusing length. The acoustic emission is detected with a differential microphone, one end of which is positioned in a measuring cell and the other end of which is positioned in a reference cell. A processor determines the concentration of the substance being measured based upon the detected acoustic signal. In order to determine the concentration of glucose in the bloodstream, the excitation source is preferably tuned to the absorption bands of glucose in spectral ranges from about 1520-1850 nm and about 2050-2340 nm to induce a strong photoacoustic emission. In these wavelength ranges, water absorption is relatively weak and glucose absorption is relatively strong.

As another example, U.S. Pat. No. 6,833,540 to MacKenzie, et al describes a system for measuring a biological parameter, such as blood glucose, the system directing laser pulses from a light guide into a body part consisting of soft tissue, such as the tip of a finger to produce a photoacoustic interaction. The resulting acoustic signal is detected by a transducer and analyzed to provide the desired parameter.

All of the above optical techniques are disadvantageous for at least the reason that they teach the application of energy to a medium without giving consideration to its acoustic oscillation properties, thus requiring relatively high laser power. Consequently, such techniques are energy inefficient, and provide an inadequate level of sensitivity.

Another prior art photoacoustic material analysis system is described in U.S. Pat. No. 6,466,806 to Geva, et al, in which the concentration of a component of interest in a medium is determined by resonant photoacoustic spectroscopy with a light pulse-train comprising equidistant short pulses having variable duration, frequency, number, and power. The light wavelength is selected so as to be absorbed by the component of interest. Upon irradiation, acoustic oscillations are generated by the absorbed light in a relatively thin layer of the medium, characterized by a heat-diffusing length. The frequency repetition of the short light pulses in the pulse-train is chosen to be equal to the natural acoustic oscillation frequency of the thin layer of the medium that can be considered as a thin membrane, such that the acoustic oscillation becomes resonant. Measuring of the amplitude and the frequency of the resonant oscillations determine the concentration of the component of interest, making the system suitable for monitoring of blood components, especially glucose.

Unfortunately, the above system, as well as the majority of prior art photoacoustic material analysis techniques, are disadvantageous. Contrary to the present invention, they teach the application of energy to a medium without giving consideration to the overlapping of absorption bands of different components, and the irregularity of elastic properties of a medium, such as human skin. Consequently, such prior art techniques provide an inadequate level of sensitivity and large errors of measuring.

BRIEF SUMMARY

Consistent with the present invention, there is provided an apparatus for determining a concentration of an analyte in tissue, comprising a first radiation source operative to emit a first radiation beam to irradiate a testing area of tissue and cause a first scattering of radiation; a second radiation source operative to emit a plurality of second radiation beams to periodically irradiate the testing area and cause a plurality of second periodic scatterings of radiation; at least two detectors for detecting the first and second scatterings of radiation and converting the detected scatterings into electrical signals; and a processor for determining the concentration of the analyte based on said electrical signals.

A method for determining a concentration of an analyte in tissue, comprising irradiating a testing area of tissue with a first radiation source emitting a first radiation beam causing an initial back-scattering of radiation and a second radiation source periodically emitting a second radiation beam to periodically irradiate the testing area causing a periodic back-scattering of radiation; detecting the initial and periodic back-scatterings; converting the detected back-scatterings into electrical signals; and determining the concentration of the analyte in response to said electrical signals and displaying the concentration.

Further consistent with the present invention, there is provided a method of calibrating an optical apparatus for determining a concentration of an analyte, comprising the steps of obtaining a sample of a fluid containing an analyte; determining a first concentration of the analyte using a fluid-based apparatus; determining a second concentration of the analyte using the optical apparatus; and determining if the second concentration is equivalent to the first concentration, wherein if the second concentration is not equivalent to the first concentration, offsetting the optical apparatus such that the second concentration is equivalent to the first concentration.

In addition, consistent with the present invention, there is also provided a probe head for use in an optical apparatus for determining a glucose concentration of a subject, the probe head comprising a plurality of fiber optic bundles communicable with a first radiation source, a radiation light source, a first detector, and a second detector; and an input/output interface for transmitting electrical signals to the first radiation source and the second radiation source, and for transmitting electrical signals from the first detector and the second detector.

Consistent with the present invention, there is also provided an apparatus for non-invasively determining a concentration of glucose in a subject using optical excitation and detection, comprising a first radiation source for emitting an exciter beam for irradiating a surface of the subject, causing at least one of physical and chemical changes in the surface, and causing an initial back-scattering of radiation; a second radiation source for periodically emitting a probe beam for irradiating a surface of the subject and cause periodic back-scattering of radiation; at least one detector for detecting the initial and periodic back-scatterings, and converting the detected back-scatterings into electrical signals of at least one of the amplitude, frequency or decay time of the physical and chemical changes, the back-scatterings being modulated by the physical and chemical changes; and a processor for determining the concentration of glucose by differentiating over time at least the amplitude, frequency or decay time of the physical and chemical changes.

Consistent with the present invention, there is further provided a method for non-invasively determining a concentration of glucose in a subject using optical excitation and detection, comprising emitting an exciter beam for irradiating a surface of the subject, causing physical and chemical changes in the surface, and causing an initial back-scattering of light; periodically emitting a probe beam for irradiating a surface of the subject and cause periodic back-scattering of light; detecting the initial and periodic back-scatterings, and converting the detected back-scatterings into electrical signals of at least the amplitude, frequency or decay time of the physical and chemical changes, the back-scatterings being modulated by the physical and chemical changes; and determining the concentration of glucose by differentiating over time at least one of the amplitude, frequency or decay time of the physical and chemical changes.

Additional features and advantages consistent with the invention will be set forth in part in the description which follows, and in part will be obvious from the description, or may be learned by practice of the invention. The features and advantages consistent with the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

BRIEF DESCRIPTION OF THE DRAWINGS

The present invention will be understood and appreciated more fully from the following detailed description taken in conjunction with the appended drawings in which.

DETAILED DESCRIPTION

Reference will now be made in detail to the exemplary embodiments of the invention, examples of which are illustrated in the accompanying drawings. Wherever possible, the same reference numbers will be used throughout the drawings to refer to the same or like parts.

Figure 1:
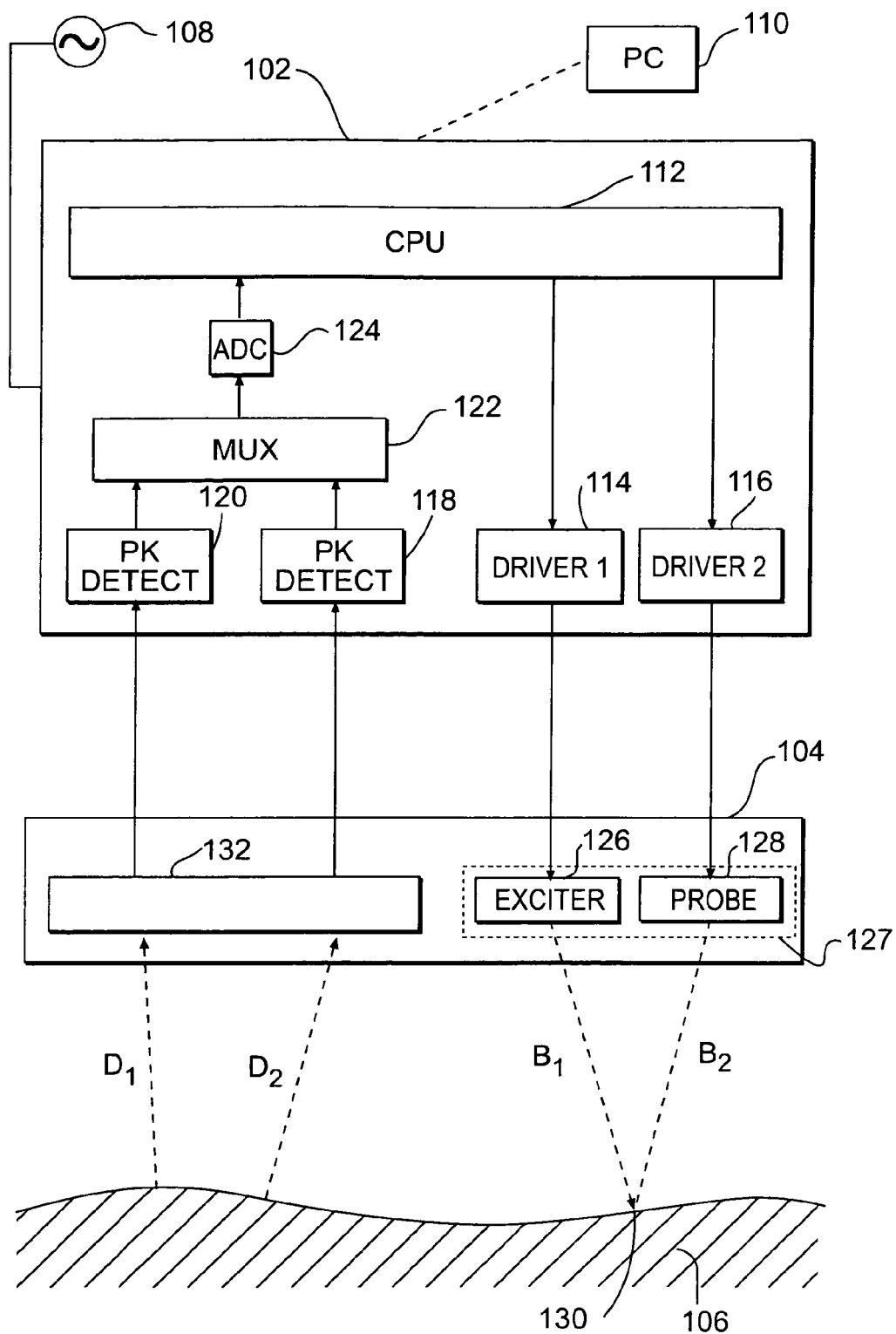
FIG. 1 is a simplified block diagram illustrating an optical apparatus for determining a concentration of an analyte, consistent with the present invention.

FIG. 1 is a simplified block diagram illustrating an optical apparatus for determining a concentration of an analyte, consistent with the present invention. As shown in FIG. 1, the optical apparatus includes an electronics enclosure 102 connected to an optical components enclosure 104. Electronics enclosure 102 may be connected to optical components enclosure 104 through conductors, wires, wirelessly, or electronics enclosure 102 and optical components enclosure 104 may be contained in a single enclosure, with electrical connection therebetween. Consistent with embodiments of the present invention, optical components enclosure 104 may comprise a probe, as further illustrated in FIG. 3.

Optical components in optical components enclosure 104 may be operable to irradiate surface 106 with radiation beams $B_1$ and $B_2$, and detect first and second scatterings of radiation $D_1$ and $D_2$. Consistent with the present invention, the optical apparatus may be connected to power source 108 for providing power to both electronics enclosure 102 and optical components enclosure 104, and components located therein. Although illustrated as an external AC power source, power source 108 may be included in either of electronics enclosure 102 or optical components enclosure 104, and may be AC or DC. Moreover, if electronics enclosure 102 and optical components enclosure 104 are connected wirelessly, a separate additional power source may be connected to optical components enclosure 104. The optical apparatus may further be connected to an external processing device 110 for displaying, monitoring, tracking results, and calibrating the optical apparatus. External processing device may comprise a personal computer (PC), a personal digital assistant (PDA), a smartphone, or other such device.

Consistent with the present invention, electronics enclosure 102 may house an array of electronic components suitable for facilitating the determination of a concentration of an analyte. For example, electronics enclosure 102 may include a processor or CPU 112, a first radiation driver 114, a second radiation driver 116, a first peak detector 118, a second peak detector 120, a multiplexer (MUX) 122, and an analog to digital converter (ADC) 124. The operation of these components will be discussed further in conjunction with the discussion of FIG. 2.

Figure 3:
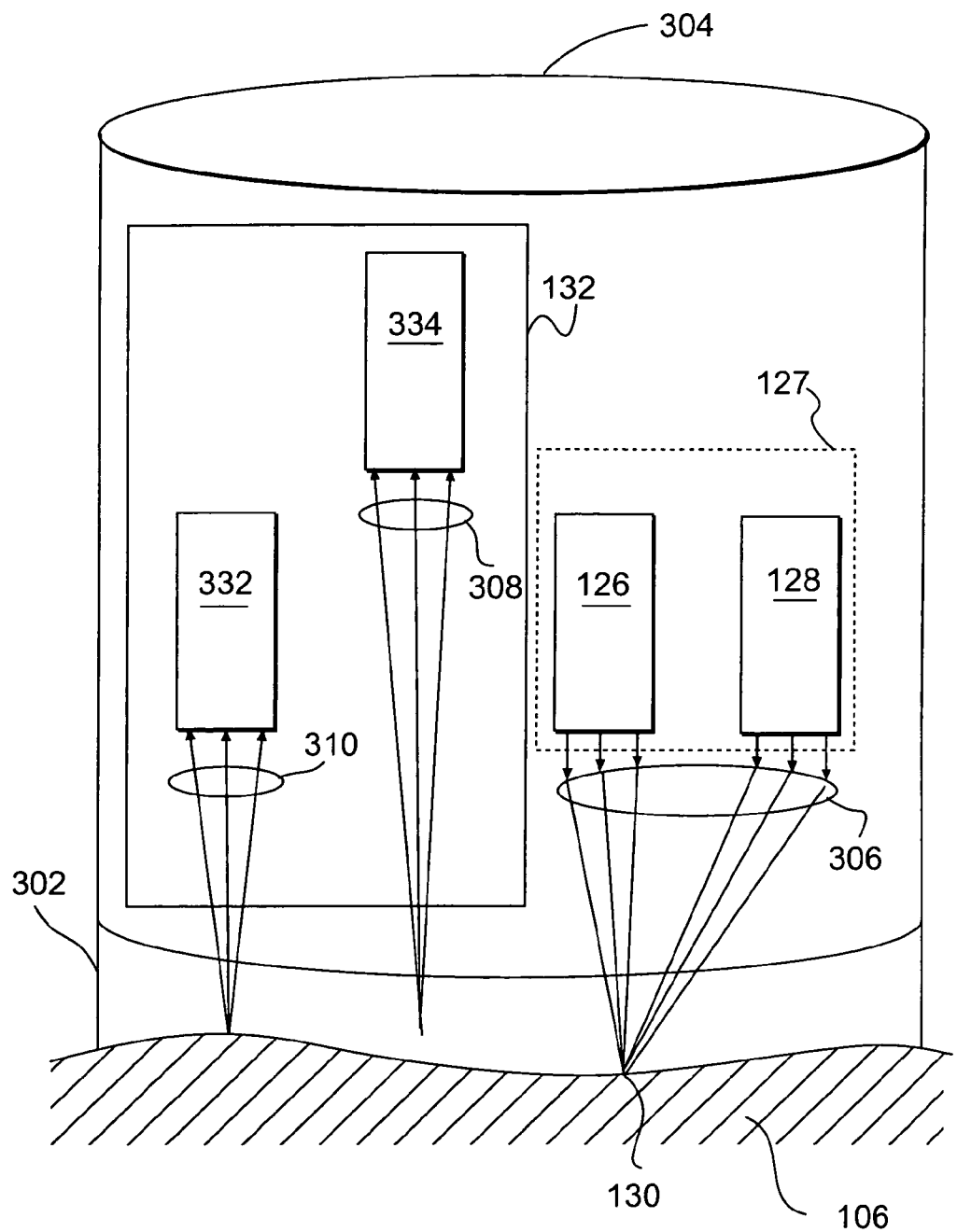
FIG. 3 illustrates an embodiment of the optical components enclosure of FIG. 1.

Similarly, optical components enclosure 104 may house an array of optical components for use in determining the concentration of an analyte. As shown in FIG. 1, optical electronics enclosure 104 may include first radiation source 126 and second radiation source 128 for irradiating a testing area 130 on surface 106 with first and second radiation beams $B_1$ and $B_2$. Consistent with the present invention, first and second radiation beams $B_1$ and $B_2$ may be emitted from a single radiation source 127 capable of generating first and second radiation beams $B_1$ and $B_2$. Optical electronics enclosure 104 may further include a detector for receiving first and second scatterings of radiation $D_1$ and $D_2$. Consistent with the present invention a single detector 132 may be configured to receive first, second, and any other scatterings of radiation. Further consistent with the present invention, detector 132 may include separate scattered radiation detectors, as shown in FIG. 3, to separately receive first and second scatterings of radiation $D_1$ and $D_2$. Consistent with embodiments of the present invention, and may include optical receiving sensors, such as a photodiode, including a P-Intrinsic-N (PIN) photodiode, an avalanche photodiode, a photoelectrical multiplier, or a photoresistor. An optical amplifier (not shown) may further be included in optical electronics enclosure 104, for amplifying the power of the first or second radiation beams. Consistent with the present invention, optical amplifier may be an optical fiber amplifier. Optical electronics enclosure 104 may also further house an optical converter (not shown) for converting wavelengths of first and second radiation beams $B_1$ and $B_2$.

First and second radiation sources used in embodiments consistent with the present invention may be selected depending on such factors as the power or wavelength of radiation needed for accurately determining the concentration of an analyte, the periodicity of the radiation needed, size constraints or cost. For example, first radiation source 126 and second radiation source 128 may be pulsed laser diodes, fiber-coupled diode laser arrays, flash lamps or pulsed fiber optical lasers. First radiation source 126 and second radiation source, or single radiation source 127, may further include combinations of these types of radiation sources. For example, in one embodiment, first radiation source 126 or second radiation source 128 may include an erbium (Er)-glass rod or slab laser pumped by additional diode lasers. In another embodiment, first radiation source 126 or second radiation source 128 may include a tunable $Co:MgF_2$ laser. In yet another embodiment, first radiation source 126 or second radiation source 128 may include a Q-switched neodymium containing optical medium laser.

Consistent with the present invention, the characteristics of the emitted radiation source used again will depend on the particular analyte being examined. That is, the power, type of radiation, wavelength, and periodicity, for example, and will affect the properties of first and second radiation beams $B_1$ and $B_2$ emitted from first radiation source 126 and second radiation source 128, and these properties will each differently affect particular analytes, and it is thus important to tailor these properties to maximize the ability of the optical apparatus to determine the concentration of the analyte. Different materials exhibit different reflectance, transmittance, and absorption properties. When performing optical measurements for determining the concentration of an analyte in a particular medium, the properties of both the analyte and the medium must be taken into consideration. The amount of radiation that is absorbed and scattered by the analyte is dependent on the power and wavelength of the radiation beams. Accordingly, it is desirable to emit radiation beams at a particular power and wavelength sufficient to produce a measurable amount of absorption and scatterings attributable to the analyte being examined, and differentiated from any surrounding mediums. For example, first and second radiation beams $B_1$ and $B_2$ will be emitted having predetermined wavelengths and a predetermined power. Consistent with embodiments of the present invention, the predetermined wavelengths and power may be the same or may be different, depending on the analyte being examined.

In a particular embodiment consistent with the present invention, first and second radiation beams $B_1$ and $B_2$ are emitted having predetermined wavelengths that are selected from a characteristic absorption band of the analyte being examined in a particular medium. In another embodiment, first and second radiation beams $B_1$ and $B_2$ are emitted at a wavelength which corresponds to a peak wavelength of an absorption band of the analyte being examined. In embodiments wherein first and second radiation beams $B_1$ and $B_2$ are emitted with different wavelengths, one beam $B_1$ or $B_2$ may have a wavelength which is greater than an absorption band peak of the analyte, and the other beam $B_1$ or $B_2$ may have a wavelength which is less than the absorption peak of the analyte. In specific embodiments, as will be described in further detail below, consistent with the present invention, a first radiation beam $B_1$ is emitted at a power of about 1-10 W and a wavelength of about 1550 nm, and a second radiation beam is emitted at a power of 0.1-1 W and a wavelength of about 1550-1690 nm.

As previously noted, first radiation source 126 and second radiation source 128 may comprise a pulsed radiation source. In embodiments using a pulsed radiation source, first and second radiation beams $B_1$ and $B_2$ may also be pulsed. For example, when using a pulsed source, first and second radiation beams $B_1$ and $B_2$ may be emitted as mono-pulses with a predetermined delay between the pulses. First and second radiation beams $B_1$ and $B_2$ may also be emitted as short pulses of quasi-continuous (QCW) light having an equal spacing therebetween, and a variable repetition rate. Furthermore, first and second radiation beams $B_1$ and $B_2$ may be emitted as a train of pulses, and having a variable frequency, a variable pulse power, a variable pulse duration, and a variable number of pulses. In a particular embodiment, noted below, second radiation beam $B_2$ is emitted as a short pulse having equal spacing, to periodically irradiate testing area 130.

Figure 2:
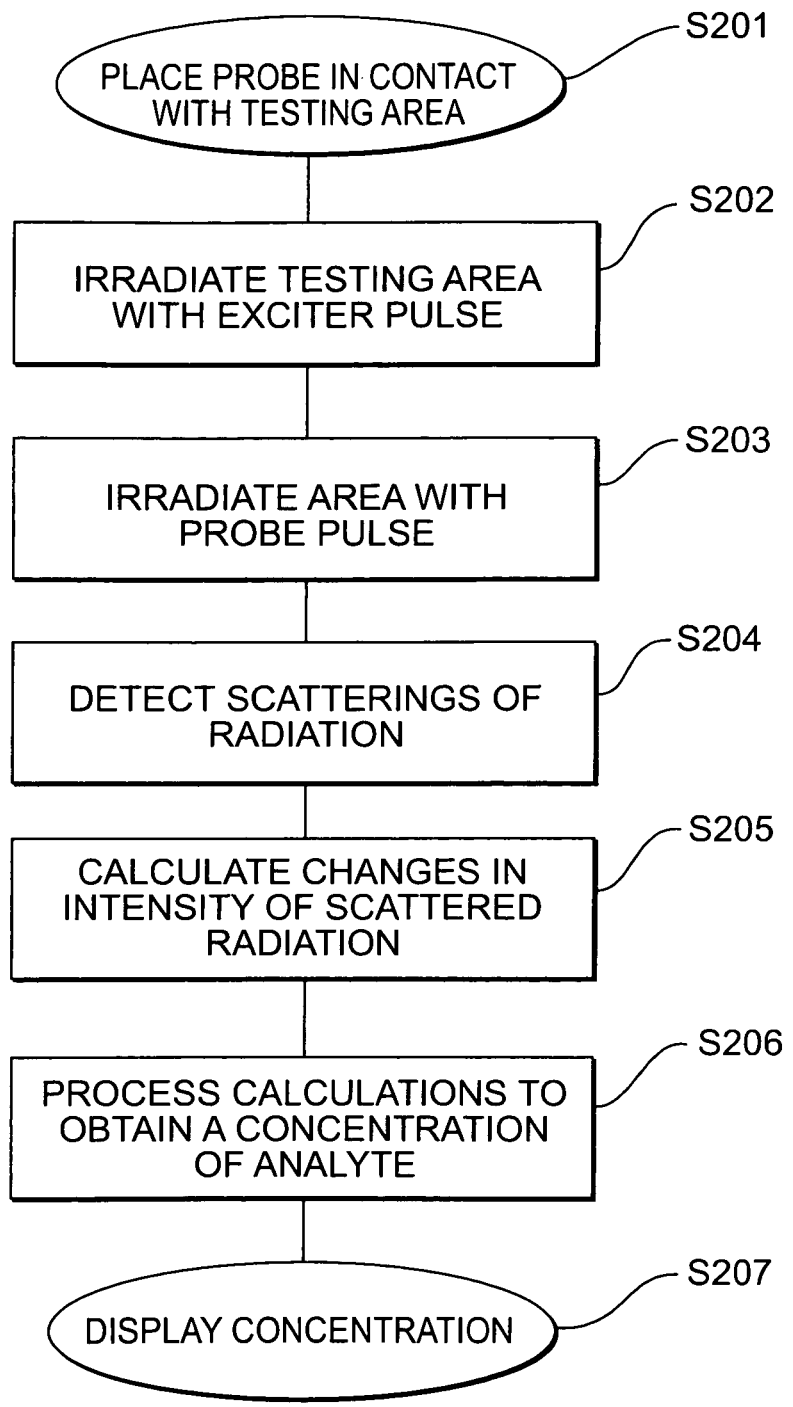
FIG. 2 is a flowchart illustrating a method for determining a concentration of an analyte, consistent with the present invention.

Reference is now made to FIG. 2, which is a flowchart illustrating a method for determining a concentration of an analyte, consistent with the present invention. In an embodiment consistent with the present invention, the method illustrated in FIG. 2 may be performed using the optical apparatus illustrated in FIG. 1. For the purpose of illustrating such an embodiment, the steps of FIG. 2 will be described in conjunction with the operation of FIG. 1.

A probe, which may be optical components enclosure 104, is initially placed in contact with testing area 130 on surface 106 (S201). Consistent with the present invention, the probe may be in contact with testing area 130, or the probe may be near testing area 130. Further consistent with the present invention, testing area 130 may be at a surface 106, or may be below surface 106. Testing area 130 is irradiated with a first radiation beam $B_1$ emitted from first radiation source 126, which may be an exciter pulse (S202). Testing area 130 is subsequently irradiated with a second radiation beam $B_2$ emitted from second radiation source 128, which may be a probe pulse (S203).

Consistent with the present invention, second radiation source 128 may emit a plurality of second irradiation beams $B_2$, each beam emitted with a predetermined period therebetween. First and second radiation beams $B_1$ and $B_2$ will irradiate testing area 130, and a predetermined amount of radiation will be back scattered from the testing area, depending on the reflectivity of surface 106, illustrated as a first scattering $D_1$ and a second scattering $D_2$. Moreover, first and second radiation beams $B_1$ and $B_2$ may further cause periodic or non-periodic transient processes in surface 106 which may at least partially modulate scatterings of radiation $D_1$ and $D_2$.

Scatterings of radiation $D_1$ and $D_2$ may then be detected by detector 132 (S204). Detector 132 converts detected scatterings $D_1$ and $D_2$ into electrical signals for processing. Consistent with the present invention, the electrical signals may represent at least one of the amplitude, frequency, or decay time of any transient processes that may be produced in surface 106. The electrical signals are then transmitted from first and second peak detectors 118 and 120 to multiplexer 122. Multiplexer 122 combines the electrical signals from first and second peak detectors 118 and 120, and outputs a single combined electrical signal to analog to digital converter 124. Analog to digital converter 124 converts the input analog electrical signal into a digital electrical signal and outputs the digital electrical signal to processor 112.

Processor 112 receives the digital electrical signals and executes instructions, which may be stored in an internal memory (not shown), for performing calculations using the digital electrical signals. For example, processor 112 may calculate changes in the intensity of scatterings of radiation $D_1$ and $D_2$ (S205), the changes in the intensity being caused by repeated emission of second radiation beams $B_2$, and any subsequent transient processes that may occur in surface 106 as a result of emitted first or second radiation beams $B_1$ and $B_2$. From the calculated changes in intensity, processor 112 will then execute instructions to perform an algorithm for calculating the concentration of an analyte present at testing area 130 (S206). Consistent with the present invention, the calculations may also be performed by an external processor, for example, a processor contained in PC 110. The calculated concentration may then be displayed for a user to view (S207). Consistent with the present invention, the concentration may be displayed on a display screen attached to electronics enclosure 102, or on computer 110. Moreover, the concentration may also be tabulated in computer 110 for trending and over-time analysis.

Consistent with the present invention, image analysis techniques may be used in conjunction with the optical apparatus described herein. In particular, image analysis techniques may be used to ensure that first and second radiation beams $B_1$ and $B_2$ are consistently incident on testing area 130, with no variation. Image analysis techniques may include video hardware and software, attached to and/or embedded on optical apparatus, which allows a user to accurately position optical apparatus such that radiation beams $B_1$ and $B_2$ are consistently incident on testing area. Consistent with the present invention, a portable video camera could be installed such that a real time video feed could show user positioning optical apparatus on surface 106. Markers could be placed at testing area 130 so that user could reliably, using the video feed, align the optical apparatus with testing area 130 to ensure incidence thereon.

FIG. 3 illustrates an embodiment of the optical components enclosure of FIG. 1. In this embodiment, optical components enclosure 104 of FIG. 1 is formed into a probe, or a probe head 304. Probe head 304 includes at least one radiation emitter, which may include first and second radiation emitters 126 and 128, at least one detector 132, which may include first and second scattered radiation detectors 332 and 334 having a different spacing with respect to surface 106 within detector 132. Probe head 304 may also include a first lens 306 for focusing radiation beams emitted from first and second radiation emitters onto test area 130. Probe head 304 may also include a second lens 308 and a third lens 310, for respectively focusing scattered radiation from surface 106 into second detector 334 and first detector 332. Although not shown in FIG. 3, probe head 304 may further be connected to other electronic processing components, such as those contained in electronics enclosure 102 shown in FIG. 1.

As shown in FIG. 3, in an embodiment consistent with the present invention, detector 132 is provided at a predetermined distance from surface 106. Consistent with the present invention second scattered radiation detector 334 may be provided in probe head 304 at a distance from surface 106 that is greater than the distance between first scattered radiation detector 332 and surface 106. By providing second scattered radiation detector 334 at a greater distance from surface 106 the optical apparatus is able to generate additional data points for performing a differential analysis on, and thus increasing the accuracy of the concentration readings. For example, for a given system excited by a first radiation beam $B_1$ and a second radiation beam $B_2$, the amplitude of detected scatterings at second scattered radiation detector 334 will be smaller than those detected at first scattered radiation detector 332, and can be used to calculate a relative amplitude between the detected scatterings at the two detectors. This relative amplitude can then be used to offset for an errors cause by positioning, pressure, or radiation source instability. Although the amplitude of the detected scatterings has been described as a detected parameter, the parameter may also be related to the frequency or decay time of the scatterings, consistent with the present invention.

In another embodiment of the present invention, probe head 304 may also include a gating sensor 302, which may be a contact, proximity, or pressure sensor. In embodiments using a contact sensor as gating sensor 302, the contact sensor must detect contact between probe head 304 and surface 106 before testing is allowed to begin, thus acting as a gate. In embodiments using a proximity sensor as gating sensor, the proximity sensor must detect that surface 106 is in a reasonable proximity to probe head 304. That is, in embodiments using a proximity sensor, the proximity sensor determines that there is a predetermined distance between surface 106 and probe head 304 before testing is allowed to begin.

In embodiments using a pressure sensor, sensor 302 must detect a predetermined pressure before proceeding with the test. As discussed above with reference to FIGS. 1 and 2, detected changes in the intensity of scattered beams $D_1$ and $D_2$ may be influenced by transient processes caused by first and second radiation beams $B_1$ and $B_2$. When placing probe head 304 in contact with surface 106, an additional transient process may be introduced into surface 106, further affecting changes in the intensity of scattered beams $D_1$ and $D_2$, and thus also affecting the calculated concentration of the analyte. A certain pressure imparted on surface 106 by probe, however, may be used as an offset such that when calculating the concentration of the analyte, the known pressure and its effects can be taken into consideration and corrected for. The pressure sensed by pressure sensor 302 between probe head 304 and surface 106 would have to be equal to a predetermined pressure before first radiation emitter 126 would emit a first radiation beam $B_1$. Pressure sensor 302 may comprise a fiber optic pressure probe.

Figure 7:
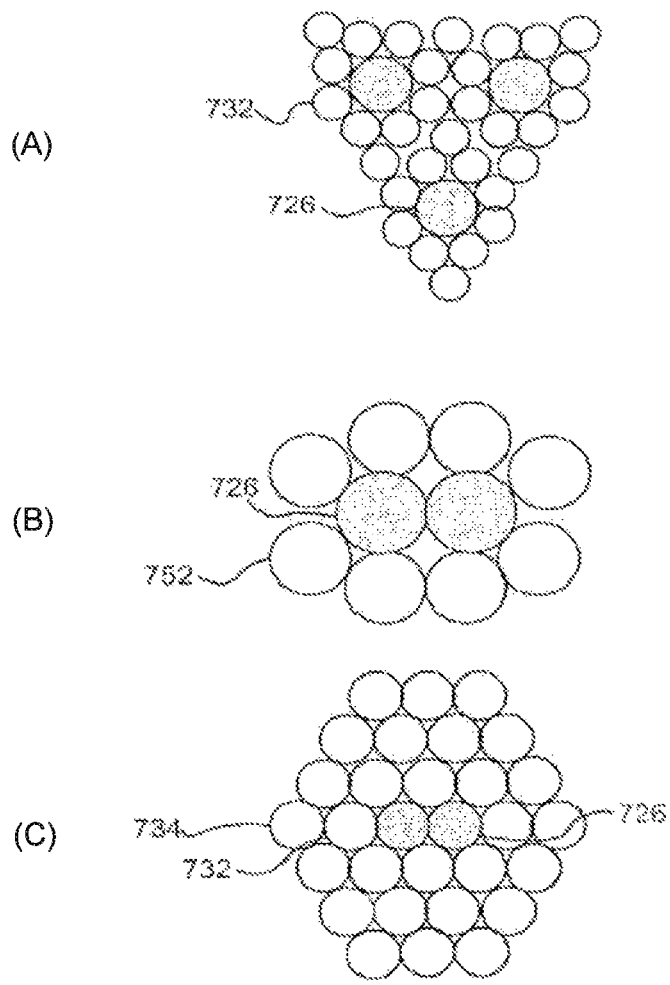
FIG. 7 illustrates examples of optical fiber arrangements consistent with the present invention

Consistent with an embodiment of the present invention, probe head 304 comprises a fiber optic probe. In this embodiment, probe head 304 is made up of many optical fibers which are in optical communication with at least one radiation source and at least one detector. For example, the optical fibers may be in optical communication with first radiation source 126, second radiation source 128, first detector 332, and second detector 334. The fiber optic bundles act as conduits or waveguides for transmitting radiation to and from surface 106. Consistent with such an embodiment, the many optical fibers may be arranged as shown in FIG. 7. The use of optical fibers allows for providing a probe head 304 which is small, lightweight, and easily able to be placed in contact with surface 106.

FIG. 7 illustrates examples of optical fiber arrangements consistent with the present invention. FIG. 7(a) illustrates an optical fiber arrangement which includes three fibers 726 for transmitting radiation from radiation source 126 and/or 128, and a plurality of pick-up fibers 732 for transmitting scattered radiation from surface 106 to a radiation detector, which may include radiation detector 132. FIG. 7(b) illustrates an optical fiber arrangement which includes two fibers 726 for transmitting radiation from radiation source 126 and/or 128, and a plurality of pick-up fibers 752 for transmitting scattered radiation from surface 106 to a radiation detector, which may include radiation detector 132. FIG. 7(c) illustrates an optical fiber arrangement which includes two fibers 726 for transmitting radiation from radiation source 126 and/or 128, and a plurality of near pick-up fibers 732 for transmitting scattered radiation from surface 106 to a radiation detector, which may include radiation detector 132 or 332, and a plurality of distant pick-up fibers 734 for transmitting scattered radiation to radiation detector 334, as shown in FIG. 3.

The optical apparatus described herein, may be used in certain embodiments to detect the concentration of glucose in human tissue. Consistent with the present invention, an embodiment for detecting glucose in human tissue emits a short, high power radiation beam $B_1$ as an exciter pulse onto testing area 130 of surface 106, which in this embodiment, is tissue. Part of the radiation is absorbed by surface 106 and generates transient processes in surface 106 which change the optical, mechanical, and other physical and chemical properties of surface 106. The change in these properties subsequently also changes the amplitude, frequency, and decay time of scattered radiation $D_1$ and $D_2$, as well as the photo-acoustic oscillations in surface 106.

After the initial emission of radiation beam $B_1$, second radiation source 128 periodically emits second radiation beam $B_2$, which acts as a probe pulse. These probe pulses typically are at a lower power than first radiation beam $B_1$, such that they only induce minimal transient processes in surface 106. The probe pulses serve to generate additional scatterings of radiation $D_1$ and $D_2$ that can be detected by detector 132 as surface 106 relaxes over time. As surface 106 relaxes from the initial high power radiation beam $B_1$, detector 132 will be able to obtain readings which can be processed to determine the amplitude of the scattered light from the initial exciter pulse, and the subsequent probe pulses, the change in amplitude of the scattered light over time, the amplitude and frequency of modulation occurring as a result of the introduced transient processes, a decay constant of surface 106, and a phase delay in amplitude modulation of light scattered from the probe pulses, which allows for calculation of the velocity of acoustical wave propagation in surface 106. From these processed values, the concentration of glucose present in surface 106 may be determined. Specific examples using optical apparatuses consistent with the present invention will be discussed in detail as follows.

Example 1

Figure 4:
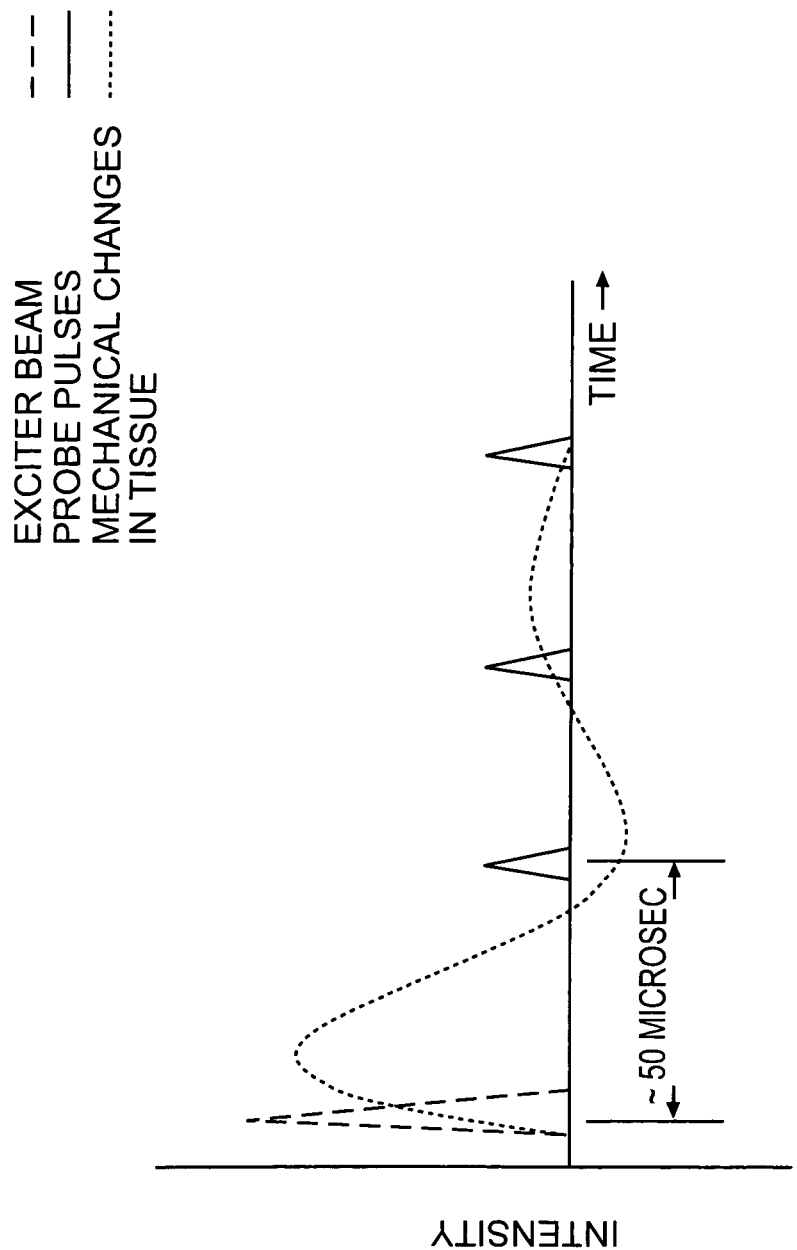
FIG. 4 is a graph illustrating the intensity and duration of the different types of radiation emitted by an optical apparatus consistent with the present invention as used in Example 1.

In an embodiment consistent with the present invention, the optical apparatus as described above with respect to FIG. 1, for example, is used to determine the concentration of glucose in a human subject, such that surface 106 of FIG. 1 is human tissue. FIG. 4 is a graph illustrating the intensity and duration of the different types of radiation emitted by an optical apparatus consistent with this embodiment. For this embodiment, first and second radiation sources 126 and 128 are selected to correspond to a glucose absorption band having a peak around 1590 nm. In this embodiment the optical apparatus is provided such that first radiation source 126 is a laser emitting an exciter beam $B_1$ at a wavelength of 1550 nm, power of 1.0-10.0 W, and a pulse width of 100 ns. Second radiation source 128 is a laser provided to emit a plurality of periodic probe pulses $B_2$ at a wavelength of 1550 nm, a power of 0.1-1.0 W, and a pulse width of 80 ns.

In operation, exciter beam $B_1$, in accordance with opto-acoustical principles, generates mechanical changes and fast-faded oscillations in tissue 106. Exciter beam $B_1$ also generates an initial scattering of light $D_1$ or $D_2$. After exciter beam $B_1$ is emitted, probe pulses $B_2$ are periodically emitted, generating additional scatterings of light $D_1$ or $D_2$. Scatterings of light $D_1$ and $D_2$ are detected by detector 132, converted to electrical signals representative of the intensity of amplitude of scatterings of light $D_1$ and $D_2$, and sent to electronics enclosure 102 for processing.

Due to the mechanical changes and fast-faded oscillations in tissue 106, the amplitude of the additional scatterings of light $D_1$ or $D_2$ changes over time. CPU 112 processes the electrical signals representative of the changes in amplitude, and sends the results to PC 110. PC 110, using a proprietary algorithm, stores the electrical signals and calculates the concentration of glucose in tissue 106.

Example 2

Figure 5:
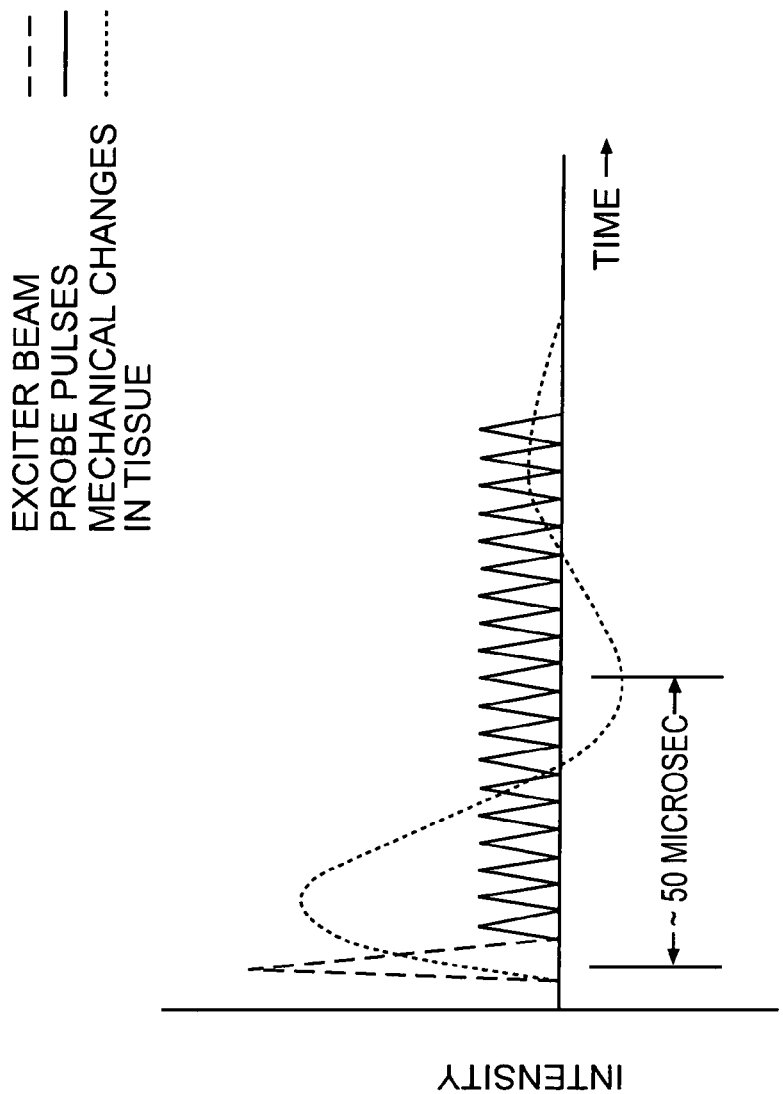
FIG. 5 is a graph illustrating the intensity and duration of the different types of radiation emitted by an optical apparatus consistent with the present invention as used in Example 2.

In another embodiment consistent with the present invention, the optical apparatus as described above with respect to FIG. 3, for example, is used to determine the concentration of glucose in a human subject, such that surface 106 of FIG. 3 is human tissue. FIG. 5 is a graph illustrating the intensity and duration of the different types of radiation emitted by an optical apparatus consistent with this embodiment. For this embodiment, first and second radiation sources 126 and 128 are selected to correspond to a glucose absorption band having a peak around 1590 nm. In this embodiment the optical apparatus is provided such that first radiation source 126 is a laser emitting an exciter beam $B_1$ at a wavelength of 1550 nm, power of 5 W, and a pulse width of 100 ns. Second radiation source 128 is a laser provided to emit a plurality of periodic probe pulses $B_2$ at a wavelength of about 1610-1690 nm, a power of 0.25-0.5 W, and a pulse width of 80 ns.

Alternatively and consistent with the present invention, exciter beam $B_1$ may be emitted at a wavelength of about 1550 nm and a power of 10 W, and periodic probe pulses $B_2$ may be emitted from the same radiation source as exciter beam $B_1$, at a wavelength of about 1550 nm and a power of about 0.25-0.5 W, with about periodic probe pulses $B_2$ being emitted such that there is about a 25 microsecond delay between each pulse.

In operation, probe head 304 is placed in contact with tissue 106. Gating sensor 302, which in this example comprises a pressure sensor, measures a pressure between probe head 304 and tissue 106. When pressure sensor 302 determines that the pressure between probe head 304 and tissue 106 is at an acceptable value, first radiation source emits an exciter beam. The exciter beam, in accordance with opto-acoustical principles, generates mechanical changes and fast-faded oscillations in tissue 106, and an initial scattering of light. After the exciter beam is emitted, probe pulses are periodically emitted by second radiation source 128, generating additional scatterings of light. The scatterings of light are detected by first and second detectors 332 and 334, converted to electrical signals representative of the intensity of amplitude of the scatterings of light, and sent to electronics enclosure 102 (shown in FIG. 1) for processing.

Due to the mechanical changes and fast-faded oscillations in tissue 106, the amplitude of the additional scatterings of light modulates over time. CPU 102 (shown in FIG. 1) processes the electrical signals representative of the changes in amplitude, and performs an algorithm for comparing the amplitudes of the scatterings of light with each other over time to look for differential changes in not only amplitude, but also frequency, decay time, and the velocity of acoustical oscillation diffusion. These differential changes are stored in an internal memory (not shown), and then used in an algorithm to calculate the concentration of glucose in tissue 106.

Figure 6:
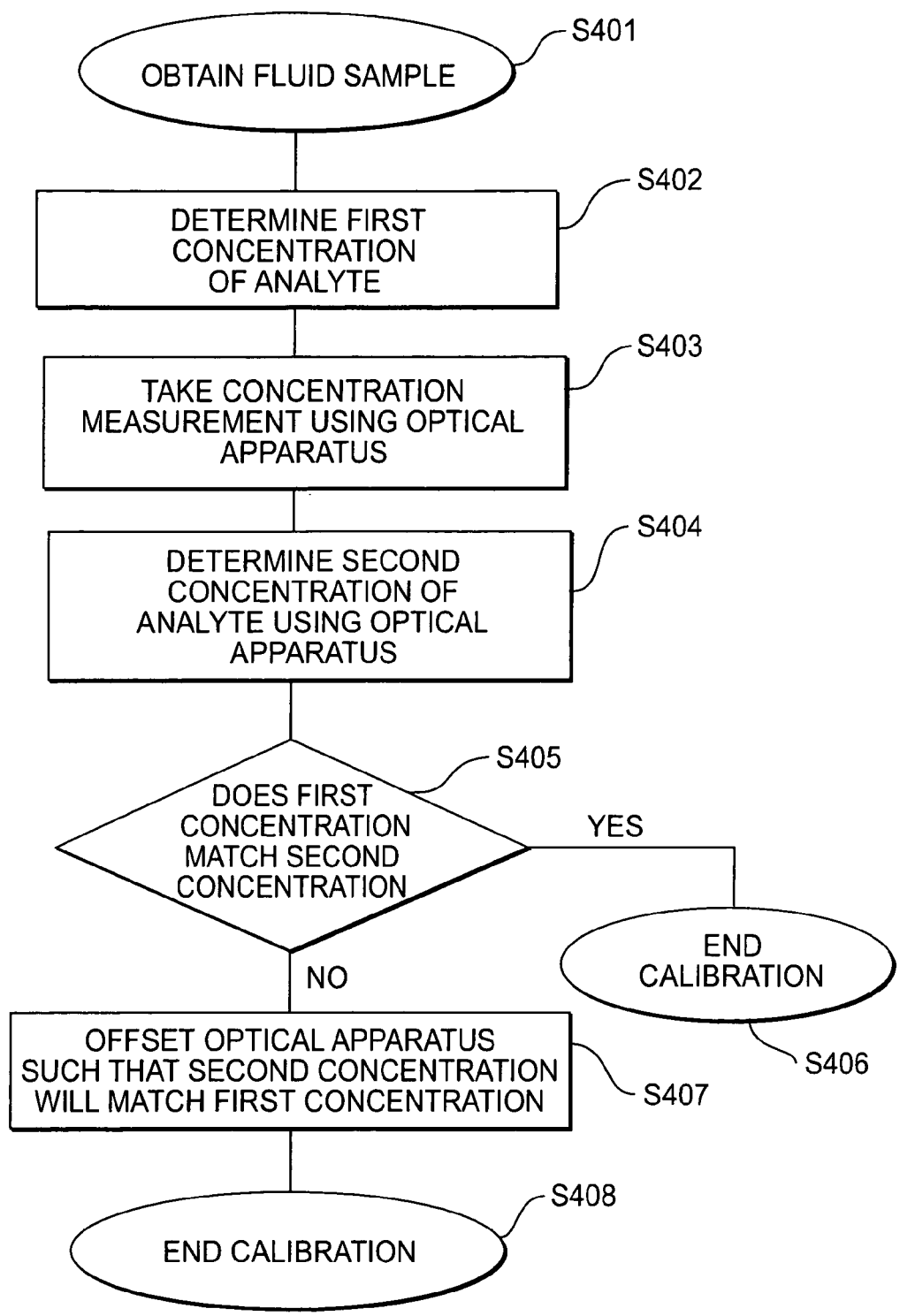
FIG. 6 is a flowchart illustrating a method for calibrating an optical apparatus consistent with the present invention.

Consistent with the present invention, although not necessarily required, the optical apparatus illustrated in FIG. 1 or 3 may be calibrated in order to provide optimal determinations of the concentration of an analyte. FIG. 6 is a flowchart illustrating a method for calibrating an optical apparatus consistent with the present invention. If the analyte being tested is glucose, as described above, it is important for the health of the user that the concentrations obtained are accurate, and in conformance with other accepted means of testing glucose concentration. Accordingly, in performing a calibration process, the results of a standard blood test is compared to the results of the optical apparatus, and the optical apparatus is offset to match the blood test. Although this calibration process has been summarized with respect to glucose testing, the calibration process described in detail below may also be used when using the optical apparatus consistent with the present invention to determine the concentration of analytes other than glucose.

First, a fluid sample is obtained (S401), and using a fluid concentration determining means, a first concentration of an analyte is determined (S402). This first concentration is recorded, and then the optical apparatus consistent with the present invention is used to take a concentration measurement (S403). The optical apparatus performs a method, such as illustrated in FIG. 2, and determines a second concentration of the analyte (S404). The first concentration and the second concentration are compared to one another to determine if they match within a predetermined degree of accuracy (S405). If the first concentration and the second concentration match, no further calibration is needed (S406). If, however, the first concentration and the second concentration do not match, the optical apparatus is offset by a predetermined amount such that the second concentration will match the first concentration (S407). After this step, the calibration is complete (S408). Consistent with embodiments of the present invention, a computer, external to the optical apparatus or on-board the optical apparatus, may perform the recordation of the concentrations, the match determination, and the offset.

While the methods and apparatus disclosed herein may or may not have been described with reference to specific hardware or software, the methods and apparatus have been described in a manner sufficient to enable persons of ordinary skill in the art to readily adapt commercially available hardware and software as may be needed to reduce any of the embodiments of the present invention to practice without undue experimentation and using conventional techniques. In addition, while the present invention has been described with reference to a few specific embodiments, the description is intended to be illustrative of the invention as a whole and is not to be construed as limiting the invention to the embodiments shown. It is appreciated that various modifications may occur to those skilled in the art that, while not specifically shown herein, are nevertheless within the true spirit and scope of the invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An apparatus for determining a concentration of an analyte in tissue, comprising:
   at least one radiation source operative to emit a first radiation beam and at least one second radiation beam, the first radiation beam irradiating a testing area of tissue and cause a first scattering of radiation, and the at least one second radiation beam having a lower intensity than the first radiation beam and periodically irradiating the testing area of tissue causing periodic second scatterings of radiation;
   at least one detector comprising a first radiation detector and a second radiation detector, the first radiation detector and the second radiation detector being configured to detect the first scattering of radiation and the second scatterings of radiation and the radiation detectors convert the detected scatterings into electrical signals, wherein the first radiation detector and the second radiation detector are located at different distances from the testing area of tissue enabling a relative amplitude between the detected scatterings to be calculated and used as an offset; and
   a processor for determining the concentration of the analyte based on said electrical signals.

2. The apparatus according to claim 1, wherein:
   the first and second radiation beams have predetermined wavelengths selected from a characteristic absorption band of the analyte in a predetermined medium.

3. The apparatus according to claim 1, wherein:
   the first and second radiation beams have predetermined wavelengths, wherein the predetermined wavelength of the first radiation beam corresponds to a peak of an absorption band of the analyte in a predetermined medium, and wherein the first radiation beam interacts with the tissue causing at least one transient process dependent on the concentration of the analyte.

4. The apparatus according to claim 1, wherein the first and second radiation beams have the same wavelength.

5. The apparatus according to claim 1, wherein the first and second radiation beams have different wavelengths.

6. The apparatus according to claim 5, wherein one of the first and second radiation beams each has a wavelength that is greater than an absorption band peak of the analyte in a predetermined medium, and one of the first and second radiation beams has a wavelength that is less than the absorption band peak of the analyte in a predetermined medium.

7. The apparatus according to claim 1, wherein the first radiation beam excites at least one periodic or non-periodic transient process in the tissue, and wherein at least one of the first and second scatterings of radiation are at least partially modulated by the at least one transient process.

8. The apparatus according to claim 7, wherein the at least one transient process includes photo-acoustic oscillations.

9. The apparatus according to claim 7, wherein the electrical signals represent at least one of the amplitude, frequency, or decay time of the at least one transient process.

10. The apparatus according to claim 1, wherein the first and second radiation beams comprise mono-pulses having a delay between the pulses.

11. The apparatus according to claim 1, wherein the second radiation beam comprises substantially equally-spaced short pulses of quasi-continuous wave (QCW) having a variable repetition rate.

12. The apparatus according to claim 1, wherein the second radiation beams comprise a train of pulses having a variable frequency, variable pulse power, variable pulse duration, and variable number of pulses.

13. The apparatus according to claim 1, wherein the first and second radiation beams are focused on the same region of the testing area.

14. The apparatus according to claim 1, wherein the first radiation beam has a power of about 1-10 W.

15. The apparatus according to claim 1, wherein the first radiation beam has a power of about 5 W.

16. The apparatus according to claim 1, wherein the first radiation beam has a wavelength of about 1550 nm.

17. The apparatus according to claim 1, wherein the second radiation beam has a power of about 0.1-1 W.

18. The apparatus according to claim 1, wherein the second radiation beam has a power of about 0.25-0.5 W.

19. The apparatus according to claim 1, wherein the second radiation beam has a wavelength of about 1610 nm to 1690 nm.

20. The apparatus according to claim 1, wherein the at least one radiation source comprises a pulsed laser diode.

21. The apparatus according to claim 1, wherein the at least one radiation source comprises a fiber-coupled diode laser array.

22. The apparatus according to claim 1, wherein the at least one radiation source comprises a pulsed optical fiber laser.

23. The apparatus according to claim 1, wherein the at least one radiation source comprises an Er-glass rod or slab laser pumped by diode lasers or a flash lamp.

24. The apparatus according to claim 1, wherein the at least one radiation source comprises a tunable Co:MgF2 laser.

25. The apparatus according to claim 1, wherein the at least one radiation source comprises a Q-switched neodymium containing an optical medium laser, and providing quasi-continuous wave generation giving equidistant short pulses having a variable duration, frequency, number and power.

26. The apparatus according to claim 1, further comprising:
an optical converter for converting wavelengths of at least one of the first and second radiation beams.

27. The apparatus according to claim 1, further comprising:
an optical fiber amplifier to increase the power of at least one of the first and second radiation beams.

28. The apparatus according to claim 1, wherein the first radiation detector and the second radiation detector comprise a photodiode.

29. The apparatus according to claim 1, further comprising an optical enclosure and an electronics enclosure wherein:
the at least one radiation source and the at least one detector is enclosed in the optical enclosure;
the processor is enclosed in the electronics enclosure; and
the optical enclosure is operably connected to the electronics enclosure.

30. The apparatus according to claim 29, wherein the optical enclosure comprises a fiber optic probe.

31. The apparatus according to claim 29, wherein the fiber optic probe comprises:
a plurality of fibers in a bundle, wherein at least one of the fibers comprises the at least one radiation source, and at least one of the fibers comprises the at least one detector.

32. The apparatus according to claim 1, wherein the apparatus is enclosed in a portable, handheld or desktop device.

33. The apparatus according to claim 32, wherein the portable device comprises a wireless communication device.

34. The apparatus according to claim 1, further comprising an optical enclosure containing the at least one radiation source and the at least one detector.

35. The apparatus according to claim 34, wherein the optical enclosure comprises a probe.

36. The apparatus according to claim 35, wherein the probe further comprises:
a contact sensor attached to the probe, the contact sensor enabling detection of engagement between the probe and the testing area, wherein if engagement is not detected, the first and second radiation sources do not emit first and second radiation beams.

37. The apparatus according to claim 35, wherein the probe further comprises:
a pressure sensor attached to the probe, the pressure sensor enabling detection of a pressure between the probe and the testing area, wherein if the detected pressure does not equal a predetermined pressure, the first and second radiation sources do not emit first and second radiation beams.

38. The apparatus according to claim 1, further comprising at least one of image analysis hardware or software for monitoring the testing area to ensure that the first and second radiation beams are incident on a predetermined location.

39. The apparatus according to claim 36, wherein the at least one of image analysis hardware or software comprises a portable video camera, and imaging software.

40. The apparatus according to claim 1, wherein the analyte is glucose.

41. A probe head for use in an optical apparatus for determining a glucose concentration of a subject, the probe head comprising:
a plurality of optical fibers coupled with at least one radiation source operative to emit a first radiation beam and at least one second radiation beam, the first radiation beam irradiating a testing area of tissue and causes a first scattering of radiation, and the at least one second radiation beam periodically irradiating the testing area of tissue causing periodic second scatterings of radiation; and at least one detector;
at least one detector comprising a first radiation detector and a second radiation detector, the first radiation detector and the second radiation detector being configured to detect the first scattering of radiation and the second scatterings of radiation and the detectors convert the detected scatterings into electrical signals, wherein the first radiation detector and the second radiation detector are located at different distances from the testing area of tissue enabling a relative amplitude between the detected scatterings to be calculated and used as an offset; and
an input/output interface for transmitting electrical signals to the at least one radiation source, and for transmitting electrical signals from the at least one detector.

42. The probe head according to claim 41, wherein the plurality of optical fibers are arranged such that fibers coupled to the at least one radiation source are surrounded by fibers coupled to the at least one detector.

43. The probe head according to claim 41, further comprising:
a pressure sensor attached to a portion of the probe head, the pressure sensor detecting a pressure between the pro be head and a surface in contact with the probe head, wherein the optical apparatus will not determine the glucose concentration of a subject unless the detected pressure is equal to a predetermined pressure.

44. The probe head according to claim 41, wherein the probe head is portable and handheld.

45. An apparatus for non-invasively determining a concentration of glucose in a subject using optical excitation and detection, comprising:
a first radiation source for emitting an exciter beam for irradiating a portion of tissue of the subject, causing at least one of physical and chemical changes to the portion of tissue, and causing an initial back-scattering of radiation;
a second radiation source for periodically emitting a probe beam for irradiating the portion of tissue and cause periodic back-scattering of radiation;
at least one detector comprising a first radiation detector and a second radiation detector for detecting the initial scattering and the periodic back-scatterings, and converting the detected back-scatterings into electrical signals of at least one of the amplitude, frequency or decay time of the physical and chemical changes, the back-scatterings being modulated by the physical and chemical changes, wherein the first radiation detector and the second radiation detector are located at different distances from the portion of tissue enabling a relative amplitude between the detected scatterings to be calculated and used as an offset; and a processor for determining the concentration of glucose by differentiating over time at least the amplitude, frequency or decay time of the physical and chemical changes.

* * * * *

UNITED STATES PATENT AND TRADEMARK OFFICE
CERTIFICATE OF CORRECTION

PATENT NO. : 9,915,608 B2
APPLICATION NO. : 12/741350
DATED : March 13, 2018
INVENTOR(S) : Peter Schultz et al.

It is certified that error appears in the above-identified patent and that said Letters Patent is hereby corrected as shown below:

In the Claims

Claim 43, Column 16, Line 46 - "pro be head" should read -- probe head --.

Signed and Sealed this
Twenty-second Day of May, 2018

Andrei Iancu
*Director of the United States Patent and Trademark Office*